United States Patent
Kirchhevel et al.

(10) Patent No.: US 11,911,224 B2
(45) Date of Patent: Feb. 27, 2024

(54) TISSUE EXPANDER

(71) Applicant: MENTOR WORLDWIDE LLC, Irvine, CA (US)

(72) Inventors: Gordon Lamar Kirchhevel, Laguna Hills, CA (US); David Henry Taffe, Irvine, TX (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 0 days.

(21) Appl. No.: 17/860,575

(22) Filed: Jul. 8, 2022

(65) Prior Publication Data
US 2022/0338950 A1  Oct. 27, 2022

Related U.S. Application Data

(62) Division of application No. 15/893,254, filed on Feb. 9, 2018, now Pat. No. 11,382,709.

(51) Int. Cl.
*A61B 90/00* (2016.01)
*A61M 5/178* (2006.01)
(Continued)

(52) U.S. Cl.
CPC ............... *A61B 90/02* (2016.02); *A61F 2/12* (2013.01); *A61M 5/178* (2013.01); *A61M 39/02* (2013.01);
(Continued)

(58) Field of Classification Search
CPC .... A61F 2/12; A61F 2250/0003; A61B 90/02; A61M 5/178; A61M 39/02;
(Continued)

(56) References Cited

U.S. PATENT DOCUMENTS

| 4,643,733 A | 2/1987 | Becker |
| 4,800,901 A | 1/1989 | Rosenberg |

(Continued)

FOREIGN PATENT DOCUMENTS

| EP | 0 391 011 A1 | 10/1990 |
| WO | 2009/023766 A1 | 2/2009 |

OTHER PUBLICATIONS

PCT Notification of Transmittal of the International Search Report and the Written Opinion of the Internationa Searching Authority, or the Declaration for International Application No. PCT/IB2019/05076 dated May 21, 2019, 7 Pages.

(Continued)

*Primary Examiner* — Todd J Scherbel
(74) *Attorney, Agent, or Firm* — Etan S. Chatlynne; Calderon Safran & Cole P.C.

(57) ABSTRACT

A tissue expander is disclosed herein. The tissue expander may comprise a shell defining a chamber, and having a flexible wall and a port disposed through the flexible wall. The shell may also include a channel disposed through the flexible wall. A first syringe containing a first volume of a liquid may be connected to the chamber of the tissue expander via the channel. A second syringe containing a second volume of the liquid may be connected to the chamber via the port at least approximately one week after the first volume of liquid is injected. The first volume of liquid may be injected more quickly than the second volume of liquid.

18 Claims, 4 Drawing Sheets

(51) Int. Cl.
  *A61M 39/02* (2006.01)
  *A61F 2/12* (2006.01)
  *A61B 17/00* (2006.01)

(52) U.S. Cl.
  CPC ............... *A61B 2017/00539* (2013.01); *A61B 2017/00557* (2013.01); *A61B 2017/00792* (2013.01); *A61B 2017/00796* (2013.01); *A61B 2017/00876* (2013.01); *A61M 2039/0205* (2013.01); *A61M 2039/027* (2013.01); *A61M 2039/0276* (2013.01)

(58) Field of Classification Search
  CPC .... A61M 2039/0205; A61M 2039/027; A61M 2039/0276
  See application file for complete search history.

(56) References Cited

U.S. PATENT DOCUMENTS

| | | | |
|---|---|---|---|
| 6,743,254 | B2 | 6/2004 | Guest et al. |
| 8,167,836 | B2 | 5/2012 | Lee et al. |
| 8,454,690 | B2 | 6/2013 | McClellan |
| 11,382,709 | B2 * | 7/2022 | Kirchhevel ............ A61B 90/02 |
| 2002/0038147 | A1 | 3/2002 | Miller, III |
| 2003/0144734 | A1 | 7/2003 | Dreschnack et al. |
| 2006/0069403 | A1 * | 3/2006 | Shalon ...................... A61F 2/12 |
| | | | 606/192 |
| 2007/0233273 | A1 | 10/2007 | Connell |
| 2013/0317610 | A1 | 11/2013 | Ledergerber |
| 2013/0325120 | A1 | 12/2013 | McClellan |
| 2016/0263358 | A1 | 9/2016 | Unger |
| 2017/0035999 | A1 | 2/2017 | Wijay |

OTHER PUBLICATIONS

Author Unknown, the Mentor CPX 4 and CPX 4 With Suture Tabs Breast Tissue Expanders, Product Insert Data Sheet, Mentor Corporate Document, May 2014, 8 Pages.

Author Unknown, Saline-Filled & Spectrum Breast Implants, Product Insert Data Sheet; Mentor Corporate Document; May 2015, 20 Pages.

Rolf E.A. Nordström, Tissue Expansion, p. 3; Published By Butterworth-Heinemann; Boston; (1996), 2 Pages.

* cited by examiner

TISSUE EXPANDER

CROSS-REFERENCE TO CO-PENDING APPLICATION

The present application is a Divisional application under 35 U.S.C. § 121 of U.S. patent application Ser. No. 15/893,254, filed Feb. 9, 2018. The entire content of this applications is incorporated by reference herein in their entirety.

FIELD

The subject matter disclosed herein relates to tissue expanders.

BACKGROUND

Tissue expanders are used to assist in stretching skin of a subject to provide a tissue pocket or capsule having an appropriate size to accommodate a permanent implant, such as a breast implant. In typical usage, the tissue expander is implanted into a subject to help prepare the subject to receive a permanent implant. The tissue expander may be expanded by introducing additional material therein, e.g., saline, until the desired size of the pocket or capsule is achieved, at which point the tissue expander may be removed. A permanent implant may then be implanted into the subject. Tissue expanders were first developed and used in human patients during the mid 1970s. Nordstrom, Rolf E. A., *Tissue Expansion* 3 (1996).

In typical use, a health care provider, likely a plastic surgeon, places a tissue expander within a tissue pocket of a subject during a surgical procedure conducted in an operating room. At that time, the tissue expander is partially filled, e.g., halfway, by a healthcare provider (e.g., the plastic surgeon or a nurse). The remaining volume gets filled gradually, over multiple office visits by the subject to her healthcare provider, such as the plastic surgeon.

SUMMARY

A tissue expander is disclosed herein. The tissue expander may comprise a shell defining a chamber, which may be a single chamber. The shell may include a flexible wall and a port disposed through the flexible wall having a first egress into the chamber. The shell may also include a channel disposed through the flexible wall having a second egress into the chamber. The port may be an injection port, such as an integrated injection port. The channel may include a valve therein. The valve may be a slitted membrane or a diaphragm valve.

The tissue expander may be used according to the following method and variations. The tissue expander may be provided. A first syringe containing a first volume of a liquid, e.g., a sterile saline solution, may be connected to the chamber of the tissue expander, e.g., via the channel. The first volume of liquid may then be injected from the first syringe into the chamber. The injection of liquid from the first syringe may be performed at a rate of between approximately 5 milliliters per second and twenty milliliters per second, e.g., at least approximately 12 milliliters per second. A second syringe containing a second volume of the liquid may be connected to the chamber via the port. A second volume of the liquid may then be injected from the second syringe into the chamber. The second volume of the liquid may be injected at least approximately one week after the first volume of liquid is injected.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
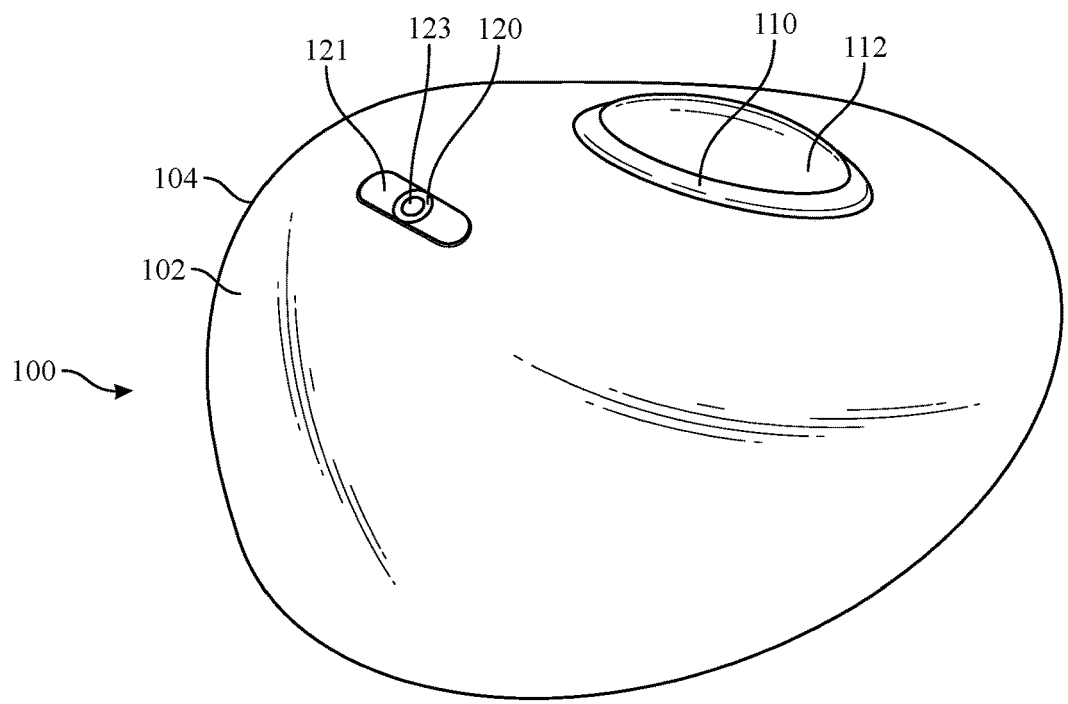
FIG. 1 depicts a perspective view of a tissue expander.
Figure 2:
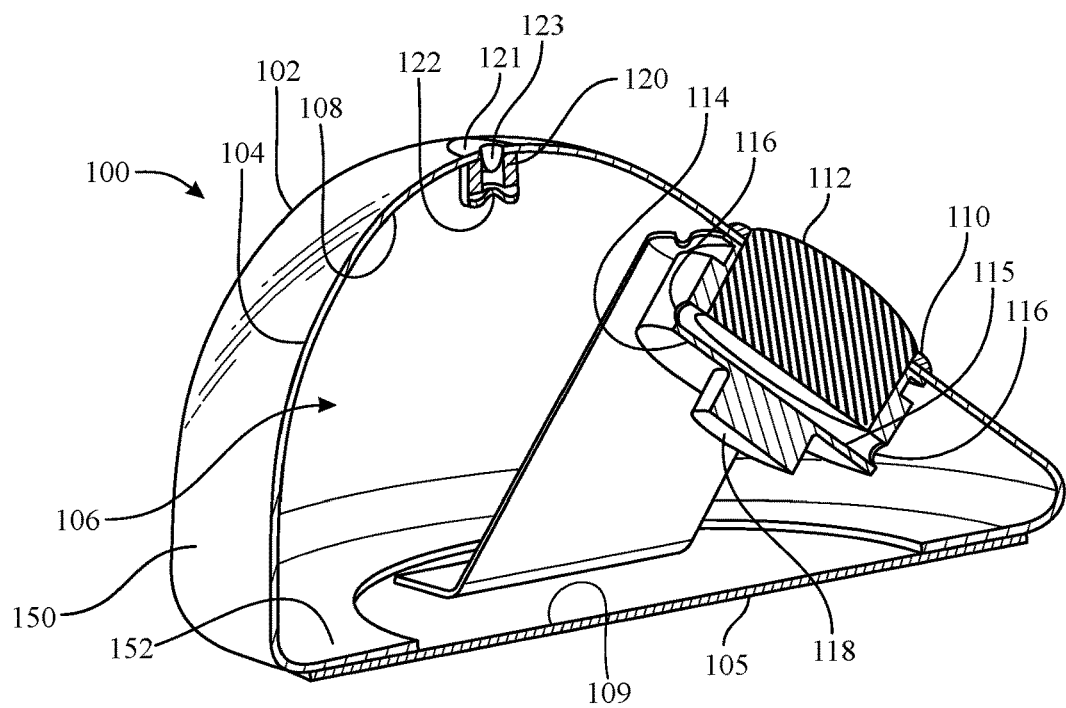
FIG. 2 depicts a cross-section view of the tissue expander of FIG. 1.

FIGS. 1 and 2 reflect a tissue expander 100 having a shell 102 comprised of a flexible (e.g., silicone rubber) wall 104 and a base 105. Flexible wall 104 comprises an upper portion 150 and a base portion 152. Base 105 contacts base portion 152 such that shell 102 defines a chamber 106 bounded by an internal surface 108 of wall 104 and an internal surface 109 of base 105. Tissue expander 100 includes a port 110 that has a membrane, e.g., injection dome 112, disposed through upper portion 150 of wall 104, to provide fluidic access between the exterior of shell 102 to chamber 106. Port 110 may preferably be a resealable integrated injection port including injection dome 112 disposed within wall 104, for example as in the CPX™4 Breast Tissue Expander manufactured by MENTOR of Irving, Texas. Alternatively, in some embodiments, the injection dome may be disposed remotely to shell 102 and connected to chamber 106 by tubing. Injection dome 112 may be fabricated from a siloxane polymer material, which has properties appropriate for allowing a surgical needle (e.g., needle 10 in FIGS. 5 and 6) to penetrate therethrough but that may be resealed after the needle is withdrawn therefrom. As shown in FIG. 2, injection dome 112 may have a cylindrical form whereby only the top portion that is exposed through wall 104 is domed. Port 110 may further include a posterior metal cup 114 disposed within chamber 106 having a diameter that is slightly smaller than the diameter of injection dome 112. The cylindrical portion of injection dome 112 may be compressed into cup 114, which compression assists in resealing injection dome 112 upon withdrawal of surgical needle 10. Cup 114 may include a hole 116, which may function as an egress for fluid to pass from port 110 and into chamber 106. Interior surface 115 of cup 114 further serves as a shield to prevent a surgical needle that has penetrated through injection dome 112 from penetrating into chamber 106, as seen in FIG. 6. Port 110 may also include a magnet 118, which may be used to locate port 110 transdermally after tissue expander 100 has been implanted.

By penetrating injection dome 112 with surgical needle 10, a fluid, e.g., air or liquid, typically a sterile liquid-saline solution, may be introduced into chamber 106 through the surgical needle, into cup 114, and out of hole 116. Thus, tissue expander 100 may be expanded by introducing fluid therein, akin to inflating a balloon. In typical usage, the surgical needle is connected to a large (e.g., 60 milliliter) syringe filled with the saline solution. The solution is passed from the syringe body and into chamber 106 by depressing the syringe's plunger to advance its piston against the solution. Upon removal of the surgical needle from injection dome 112, the compression forces upon injection dome 112 from cup 114 squeeze the hole created by the needle, effectively sealing it to prevent the solution from passing out of chamber 106 via this hole. To avoid the likelihood that the compression forces do not seal the hole created by the needle, needles 21 gauge and smaller are typically used. Such needles have an inner diameter of approximately 0.02 inches or less and an outer diameter of approximately 0.03 inches or less.

Figure 3:
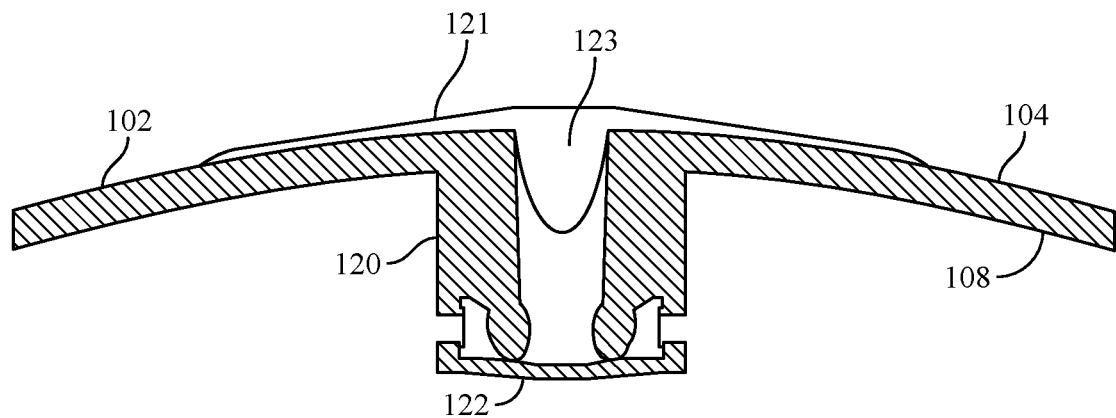
FIG. 3 depicts a magnified cross-section view of a portion of the tissue expander of FIG. 1 having a channel with a diaphragm valve in a closed configuration.
Figure 4:
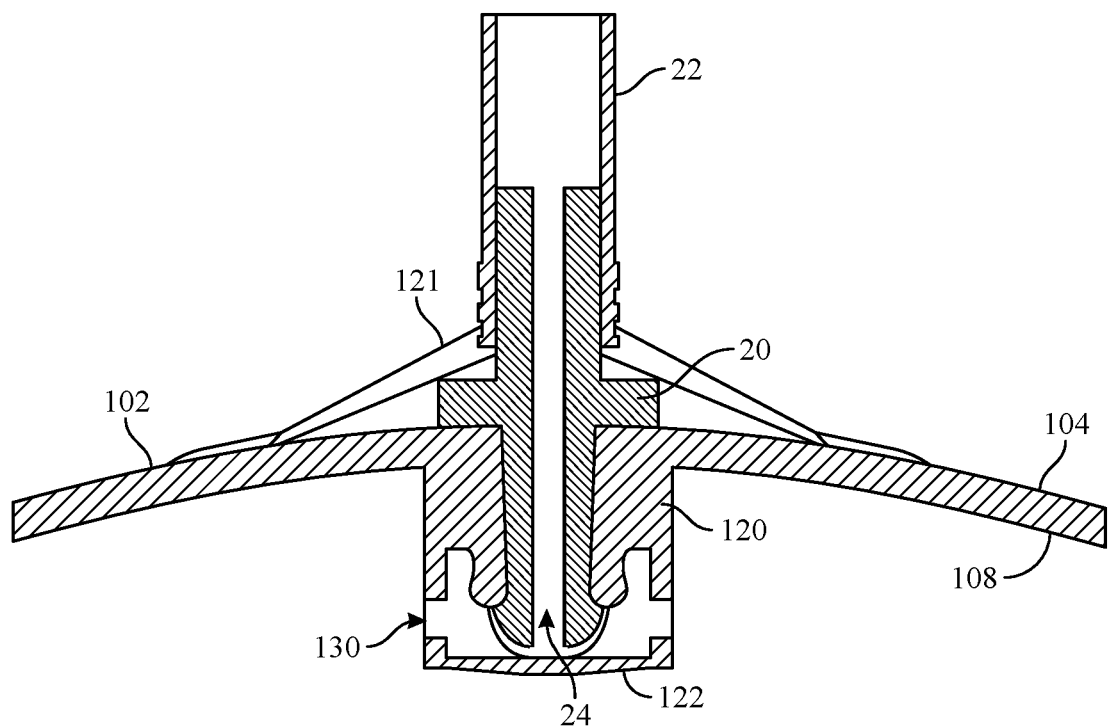
FIG. 4 depicts a magnified cross-section view of a portion of the tissue expander of FIG. 1 in which the diaphragm valve is in an open configuration.

A channel 120 may also be disposed through upper portion 150 of flexible wall 104 to provide fluidic access from outside of shell 102 into chamber 106. Channel 120 may include therein a slitted membrane or a valve 122, such as a slit valve, an X-fragm valve, or a diaphragm valve. As shown in FIGS. 3 and 4, membrane or valve 122 is a diaphragm valve. Channel 120 may also include a plug 123 that may be removably disposed within channel 120. Plug 123 may be attached to wall 104 by a band, e.g., elastic band 121, such that upon removal of plug 123 from channel 120, plug 123 cannot be lost and may be easily reinserted into channel 120. Membrane or valve 122 may have a normally closed configuration as shown in FIG. 3. Membrane or valve 122 may be placed into an open configuration by removing plug 123 from channel 120 and inserting a finger or stylet 20 into channel 120 as shown in FIG. 4. In FIG. 4, plug 123 is hidden by stylet 20. Stylet 20 may include an internal passage 24 and be connected to a tube 22 such that fluidic access to chamber 106 may be provided through tube 22, stylet 20, channel 120, and openings or egress 130 of valve 122. Channel 120 may have an inner diameter that is between approximately 0.04 inches and 0.3 inches and passage 24 of stylet 20 may have a diameter that is between approximately 0.03 inches and 0.25 inches. In typical usage, tube 22 may be connected to a large (e.g., 60 milliliter) syringe filled with saline solution. The solution is passed from the syringe body and into chamber 106 by depressing the syringe's plunger to advance its piston against the solution, which drives the solution through tube 22, stylet 20, and channel 120. Upon removal of stylet 20 from channel 120, membrane or valve 122 returns to the closed configuration (FIG. 3), preventing the solution from passing out of chamber 106 via channel 120. Plug 123 may be reinserted into channel 120.

Port 110 and channel 120 serve as two independent pathways for introducing fluid into chamber 106. Because shell 102 is fabricated from a flexible material, e.g., silicone rubber, shell 102 may be expanded by introducing fluid into chamber 106. Accordingly, tissue expander 100 may be used to expand a tissue pocket within a subject. For example, tissue expander 100 may be used in a human mastectomy patient who may require tissue expansion to prepare a breast pocket for introduction of a breast implant therein.

Tissue expander 100 may be fabricated in various sizes and shapes, usually depending on the amount that the breast pocket should be expanded based on the size of the intended breast implant. Thus, tissue expander 100 may be designed to be filled from between approximately 200 milliliters to approximately 1500 milliliters. As noted, large, e.g., 60 ml, syringes, are typically used to fill tissue expanders. Accordingly, the syringe must be filled and refilled between approximately four times to approximately twenty-five times to fill the tissue expander.

Tissue expander 100 may be, and typically is, partially filled, e.g., to approximately half of its full volume, during a surgical procedure in operating room. Although this fill may be performed using either port 110 or channel 120, the fill may be accomplished substantially faster via channel 120 because a 21 gauge surgical needle provides a greater restriction to flow than does stylet 20.

Figure 5:
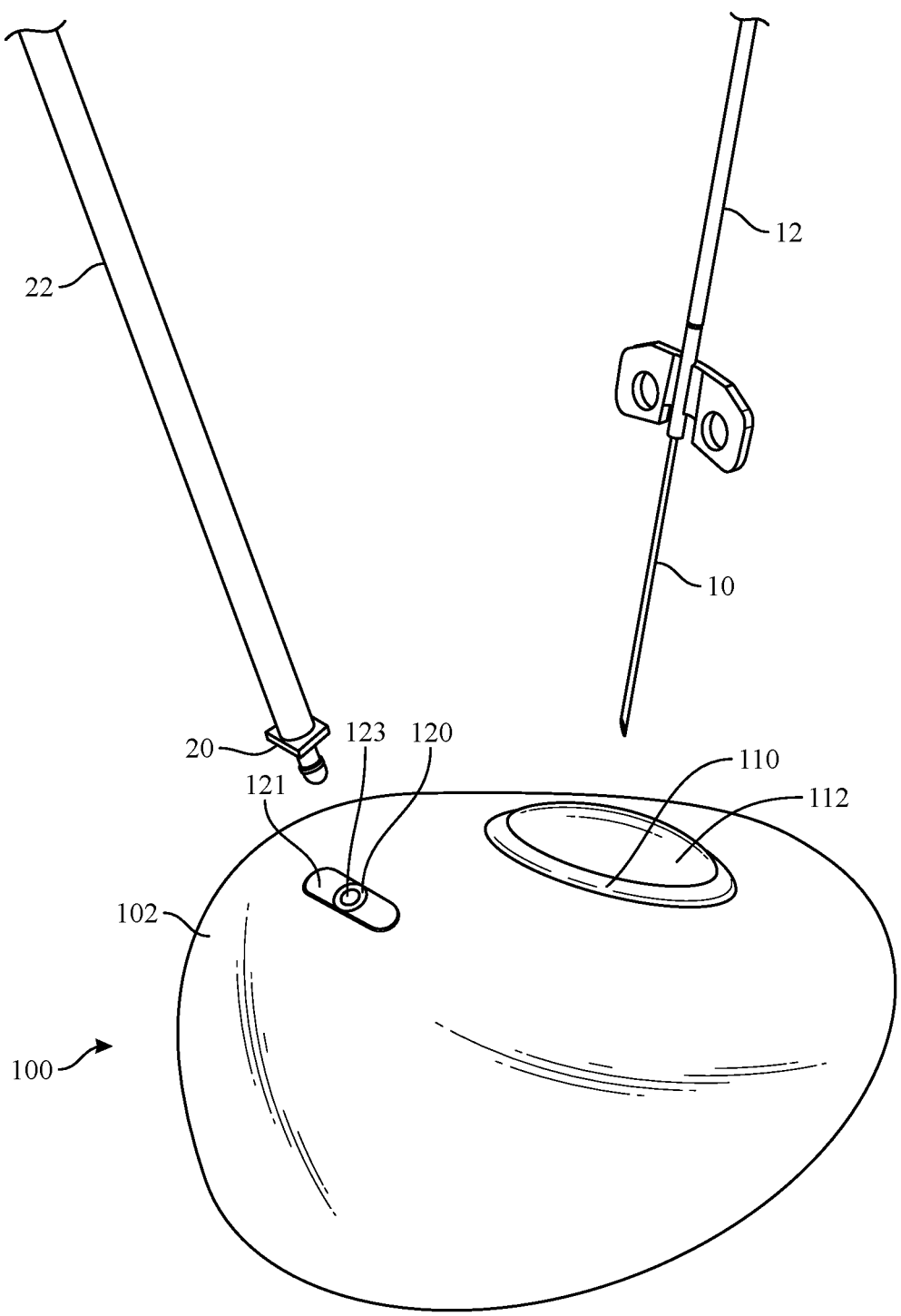
FIG. 5 depicts a perspective view of the tissue expander of FIG. 1 alongside a stylet and a surgical needle.
Figure 6:
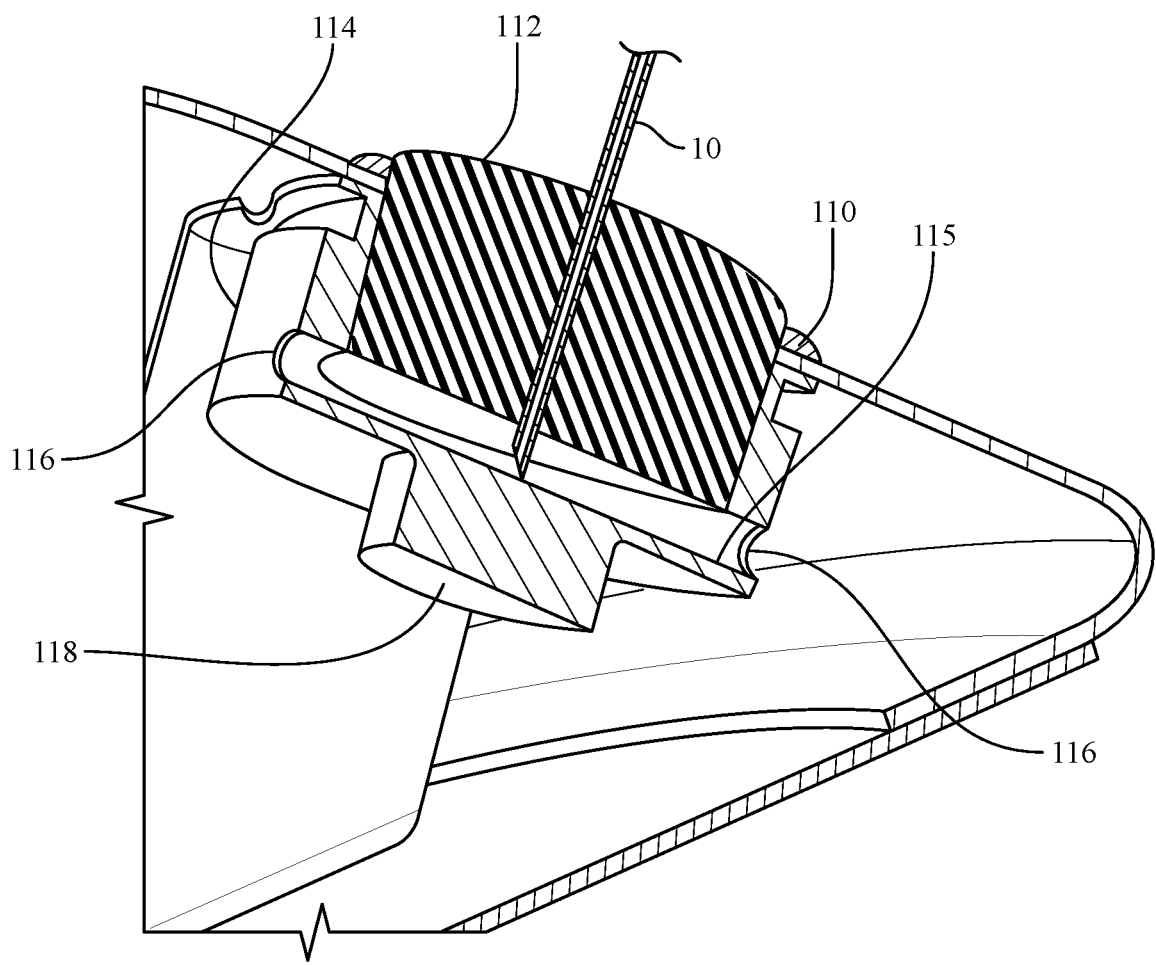
FIG. 6 depicts a magnified cross-section view of a portion of the tissue expander of FIG. 1 having an injection port with the surgical needle disposed therethrough.

FIG. 5 shows tissue expander 100 alongside a surgical needle 10 connected to a first fill tube 12 and stylet 20 connected to a second fill tube 22. Needle 10 may be used to puncture injection dome 112 of port 110, and passed therethrough, to provide fluid access between needle 10 and chamber 106. Stylet 20 may be inserted into channel 120 to open valve 122 and provide fluid access between stylet 20 and chamber 106. The structures in FIG. 5 are shown to scale or approximately to scale. Tissue expander 100 is a 450 ml expander that has a width of approximately 5.5 inches. Needle 10 is a 21 gauge needle that is approximately 1.75 inches long. Stylet 20 is 0.8 inches long and has an internal diameter of approximately 1/16 inch. It should thus be apparent to one of ordinary skill in the art that needle 10 provides a greater restriction to flow than does stylet 20.

The inventor has determined that the time it takes for a person, e.g., doctor or nurse, to inject 60 ml of saline from a 60 ml syringe into chamber 106 via a 21 gauge surgical needle 10 may be at least approximately 40 seconds. However, it may take closer to five seconds to inject 60 ml of saline from the same syringe into chamber 106 via stylet 20. Of course, these times depend on the strength of the individual who is injecting the fluid from the syringe into the chamber and how hard that individual pushes on the plunger of the syringe. However, these times may be considered rough estimates of what most healthy individuals performing the injections would accomplish. Based on these numbers, the chamber may be filled at a rate of approximately 1.3 milliliters per second via needle 10 through port 110, whereas the chamber may be filled at a rate of approximately 12 milliliters per second via stylet 20 through channel 120. These rates may be increased or decreased by changing the dimensions of surgical needle 10 and stylet 20. For example, the diameter of passage 24 through stylet 24 may be increased to reduce restriction to flow therethrough, or may be reduced to increase the restriction to flow therethrough, such that chamber may be filled at a rate of between approximately 5 milliliters per second and 20 milliliters per second.

Thus, filling tissue expander during a surgical procedure via channel 120 and stylet 20 enables substantial time savings relative to filling via needle 10 and port 110. For example, when two 480 ml tissue expanders are to be implanted (one in the left breast pocket and another in the right breast pocket) and filled halfway in the operating room before implantation using a 60 ml syringe, a total of 480 ml of saline will be injected from the 60 ml syringe. This means that a user must fill the syringe with saline and then inject the saline into chamber 106 eight times. For injection through needle 10 and port 110, the time to do the eight rounds of injecting should be at least approximately 320 seconds, which is over five minutes. For injection through stylet 20 and channel 120, the time to do the eight rounds of emptying should be closer to 40 seconds, which is less than one minute. Furthermore, filling via stylet 20 and channel 120 should fatigue the doctor's or nurse's hands substantially less than filling via a needle 10 and port 110 because advancing fluid through the needle takes more time and energy than it does through stylet 20. Thus, filling through channel 120 may help avoid injury to the doctor's or nurse's hands.

After the tissue expander has been expanded to an appropriate volume during a surgical procedure, stylet 20 may be removed from channel 120, and the implantation procedure may be completed. The patient may then visit her doctor on an outpatient basis to have the remaining volume of chamber 106 filled transdermally via port 110. Typically, the remaining volume of chamber 106 is filled over multiple outpatient visits that may occur at various intervals, e.g., approximately every week or two weeks, beginning approximately one or two weeks after the implantation procedure.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of using a tissue expander, comprising:
    providing the tissue expander, the tissue expander comprising
        a shell defining a chamber, the shell including a flexible wall,
        a port disposed through the flexible wall having a first egress into a single chamber, and
        a channel disposed through the flexible wall having a second egress into the single chamber;
    first injecting a first volume of a liquid into the single chamber via the channel; and
    at least approximately one week after the operation of first injecting the first volume of the liquid, second injecting a second volume of the liquid into the single chamber via the port.

2. The method of claim 1, wherein the operation of first injecting the first volume of the liquid comprises injecting the first volume of the liquid at a rate of between approximately 5 milliliters per second and twenty milliliters per second.

3. The method of claim 2, wherein the first volume of the liquid is injected at a rate of at least approximately 12 milliliters per second.

4. The method of claim 3, wherein the operation of first injecting the first volume of the liquid comprises connecting a first syringe to the channel.

5. The method of claim 4, wherein the operation of second injecting the second volume of the liquid comprises connecting a second syringe via the port.

6. The method of claim 1, wherein the operation of second injecting the second volume of the liquid is performed transdermally.

7. The method of claim 6, further comprising third injecting a third volume of the liquid into the chamber via the port at least approximately one week after the operation of second injecting the second volume of the liquid.

8. The method of claim 1, wherein the operation of first injecting the first volume of the liquid is performed during a surgical procedure that is completed before the operation of second injecting the second volume of the liquid is performed.

9. The method of claim 1, wherein the operation of first injecting the first volume of the liquid into the chamber via the channel is performed in an operating room and the operation of second injecting the second volume of the liquid is performed in an outpatient setting.

10. The method of claim 1, wherein the shell further comprises a base and the flexible wall of the shell includes an upper portion and a base portion with the base portion of the flexible wall contacting the base of the shell, such that the shell defines the single chamber bounded by an internal surface of the flexible wall and an internal surface of the base.

11. The method of claim 10, wherein the port is disposed through the upper portion of the flexible wall and includes the first egress into the single chamber.

12. The method of claim 11, wherein the channel is disposed through the upper portion of the flexible wall and includes the second egress into the single chamber.

13. The method of claim 12, wherein the port and the channel are not disposed through the base.

14. The method of claim 12, wherein the port comprises an injection port.

15. The method of claim 14, wherein the injection port comprises an integrated injection port.

16. The method of claim 14, wherein the channel includes a valve disposed therein.

17. The method of claim 16, wherein the valve comprises a slitted membrane in a closed configuration.

18. The method of claim 16, wherein the valve comprises a diaphragm valve.

* * * * *